United States Patent
Cho et al.

(10) Patent No.: US 8,160,685 B2
(45) Date of Patent: Apr. 17, 2012

(54) ADAPTIVE PEAK DETECTION SYSTEM AND METHOD FOR HEART PULSE

(75) Inventors: Jungdong Cho, Gyeonggi-do (KR); Myungsuk Choi, Gyeonggi-do (KR); Sangwon Lee, Seoul (KR)

(73) Assignee: Sungkyunkwan University Foundation for Corporate Collaboration, Suwon, Gyeonggi-Do (KR)

( * ) Notice: Subject to any disclaimer, the term of this patent is extended or adjusted under 35 U.S.C. 154(b) by 816 days.

(21) Appl. No.: 11/707,296

(22) Filed: Feb. 16, 2007

(65) Prior Publication Data

US 2008/0161706 A1     Jul. 3, 2008

(30) Foreign Application Priority Data

Dec. 27, 2006   (KR) .................. 10-2006-0135218

(51) Int. Cl.
*A61B 5/0452* (2006.01)
(52) U.S. Cl. .................. 600/515; 600/509; 600/512
(58) Field of Classification Search .................. 600/512, 600/515, 509; 607/14
See application file for complete search history.

(56) References Cited

U.S. PATENT DOCUMENTS

| | | | |
|---|---|---|---|
| 5,709,215 A * | 1/1998 | Perttu et al. | 600/521 |
| 6,169,918 B1 * | 1/2001 | Haefner et al. | 600/509 |
| 6,345,199 B1 * | 2/2002 | Thong | 607/5 |
| 6,539,259 B1 * | 3/2003 | Weinberg et al. | 607/9 |
| 2002/0165587 A1 * | 11/2002 | Zhang et al. | 607/28 |

FOREIGN PATENT DOCUMENTS

| | | |
|---|---|---|
| KR | 0229013A 0 | 9/1996 |
| KR | 1020020028539 A | 4/2002 |
| KR | 10-2004-0095309 | 11/2004 |

OTHER PUBLICATIONS

KIPO's Office Action and English Translation Thereof, Application No. 10-2006-0135218, 2008.

* cited by examiner

*Primary Examiner* — Carl H Layno
*Assistant Examiner* — Natasha Patel
(74) *Attorney, Agent, or Firm* — Edwards Wildman Palmer LLP

(57) ABSTRACT

The present application discloses an adaptive system and a method for detection of heartbeat peaks. The adaptive detection system for heartbeat peaks includes: means for detecting peaks of ventricular or atrial heartbeat signals; and means for determining heart conditions according to a detected peak interval. Heart beats can be detected at a low supply voltage, diseases can be determined according to the detected cardiogram signals, and treatment can be performed by diagnosis in the event of abnormality.

10 Claims, 5 Drawing Sheets

ADAPTIVE PEAK DETECTION SYSTEM AND METHOD FOR HEART PULSE

CROSS-REFERENCE TO RELATED APPLICATION

The present application claims, under 35 U.S.C. §119(a), the benefit of Korean Patent Application No. 10-2006-0135218, filed Dec. 27, 2007, the entire contents of which are hereby incorporated by reference.

BACKGROUND OF THE INVENTION

1. Field of the Invention

The present invention relates to an adaptive detection system and method for heartbeat peaks, which has a one-chip function to measure biopotential for the treatment of bradyarrhythmia caused by heart disease, and more particularly, to an adaptive detection system and method for heartbeat peaks, which can detect heartbeats to determine any diseases according to detected heartbeat signals and allow treatment by diagnosis.

2. Background Art

In general, a heartbeat detection module or system for the treatment of bradyarrhythmia caused by heart disease has a one-chip function for measuring biopotential, and includes a pair of electric leads attached to body regions of a patient above the heart to detect heartbeats and produce corresponding electro stimulations.

Examples of the heartbeat signal detection system are disclosed in Japanese Patent Application Publication Hei 08-229013, published Sep. 10, 1996, and Korean Patent Application Publication 2002-0028539, published Apr. 17, 2002.

That is, Japanese Patent Application Publication Hei 08-229013 discloses a heart pulse signal detection system as shown in FIG. 1. This detection system includes an amplifier 2 for amplifying an output from a pulse wave sensor 1, a low pass filter 3 for selectively passing a low frequency component of a pulse wave, a sample hold circuit 4 for sampling the low frequency component of the pulse wave for a predetermined period, an A/D converter for digitalizing an analog signal, a CPU 6 for receiving an output from the A/D converter 5, a keyboard 7 for acting as an input means of the CPU 6, a timer 8 having a clock generator and a counter, a memory 9 composed of a Read Only Memory (ROM) and a Random Access Memory (RAM) and an output device 10 for outputting a calculation result from the CPU 6. It is also described that the detection system can estimate electrocardiogram R-R intervals and their variations without having to use an electrocardiograph.

With this system, it is possible to easily produce a heartbeat wave R-R interval, the mean heartbeat wave R-R interval and the standard deviation of heartbeat wave R-R intervals. Since the heartbeat wave is transferred at a very high rate and transferred to the body weight substantially simultaneously with heart beating, the heartbeat wave R-R interval is presented to be equivalent with an electrocardiogram R-R interval.

In addition, Korean Patent Application Publication 2002-0028539 discloses an automatic system for heartbeat detection and emergency notification, as shown in FIG. 2, which includes an electrode 11, an amplification filter 12, a pulse wave shaper 13 and a pulse signal transmitter 14. This system monitors the condition of a patient, onto which the system is attached, for 24 hours by using electrocardiogram signals originating from heartbeats of the patent, and thus aids in managing the patient's condition. This system is designed to count the heartbeat number by detecting the electrocardiogram signals, which are produced from the heartbeats of the patient's body, in order to manage the patient's condition for 24 hours as well as to automatically generate an emergency signal in the event of an abnormal condition.

That is, the system stores heartbeat data in a memory for a predetermined time period, collects data by a data collector in the form of a database, analyzes the condition of the patient, and precedently proceeds to take the appropriate measure according to the patient's condition.

SUMMARY OF THE INVENTION

However, Japanese Patent Application Publication Hei 08-229013 has the drawback of consuming a large amount of supply voltage since it samples all voltages the same as or larger than a preset threshold voltage in the A/D conversion of cardiogram signals. Korean Patent Application Publication 2002-0028539 also has the drawback of consuming a large amount of supply voltage since it removes noise from heartbeat signals by an amplification filter and thus the circuit operates in response to the noise.

Accordingly, the present invention has been made to solve the above-mentioned problems occurring in the prior art, and an object of the present invention is to provide an adaptive system and method for detecting heartbeat peaks which is equipped with an adaptive pattern part and uses a threshold level to detect an adaptive pattern in response to an input pattern so that influences of ventricular signals can be prevented, thereby operating at a low supply voltage.

Another object of the invention is to provide an adaptive system and method for detecting heartbeat peaks which can output a prescription for a corresponding disease for the purpose of the treatment of bradyarrhythmia caused by heart disease.

In order to accomplish this object, there is provided an adaptive detection system for heartbeat peaks comprising: means for detecting peaks of ventricular or atrial heartbeat signals; and means for determining heart conditions according to a detected peak interval.

In the adaptive detection system, the peak detecting means is adapted to detect the peaks of the ventricular or atrial heartbeat signals according to an adaptive threshold level.

In the adaptive detection system, the heart condition determining means is adapted to detect and store peak interval, peak time, number of ventricular signals between atrial signals, number of atrial signals between ventricular signals, interval between ventricular and atrial peaks and far field heartbeat wave, according to the peak detected by the peak detecting means.

In the adaptive detection system, the heart condition determining means is adapted to output judgment on Ventricular Tachycardia (VT), Fast Ventricular Tachycardia (FVT), Ventricular Fibrillation (VF), Atrial Tachycardia-Atrial Fibrillation (AT-AF), Fast Atrial Tachycardia-Atrial Fibrillation (FAT-AF).

In the adaptive detection system, the peak detecting means and the heart condition determining means are realized in one chip.

In the adaptive detection system, the chip is transplantable to treat bradyarrhythmia.

In the adaptive detection system, the peak detecting means is adapted to adaptively detect the adaptive threshold level according to the heartbeat signal to determine peak time.

In the adaptive detection system, the peak detecting means is adapted to set a fixed minimum threshold level and, if a detected signal does not exceed the minimum threshold level, skip peak detection therefrom.

In the adaptive detection system, the peak detecting means detects a second peak while decreasing the threshold level by five (5) levels per second at a time point of 200 ms from a time point of peak detection.

In order to accomplish this object, there is also provided an adaptive detection method for heartbeat peaks comprising steps of: detecting peaks of ventricular and atrial heartbeat signals; and determining heart diseases according to the peak detected in the peak detecting step, wherein the detecting step comprises, upon detecting a first peak, detecting a second peak while decreasing the threshold level by five (5) levels per second at a time point of 200 ms from the detection of the first peak.

In the adaptive detection method, the determining step comprises detecting and storing peak interval, peak time, number of ventricular signals between atrial signals, number of atrial signals between ventricular signals, interval between ventricular and atrial peaks and far field heartbeat wave, according to the peak detected by the peak detecting means.

In the adaptive detection method, the determining step comprises outputting judgment on Ventricular Tachycardia (VT), Fast Ventricular Tachycardia (FVT), Ventricular Fibrillation (VF), Atrial Tachycardia-Atrial Fibrillation (AT-AF) and Fast Atrial Tachycardia-Atrial Fibrillation (FAT-AF).

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

The foregoing and other objects and features of the invention will be more apparent to those skilled in the art upon reading and understanding the description of the invention and the accompanying drawings.

Prior to the detailed description of the invention, the concept of the invention will be discussed.

The invention proposes a peak detection unit having a one-chip structure for measuring biopotential in order to detect or sense signals at a low voltage. In general, when a sensor detects an atrial signal, it also detects a faint ventricular signal.

This as a result requires a special algorithm in order not to detect any unnecessary ventricular signal. According to the invention, an atrial signal is detected as a threshold level, and then the threshold level is maintained at the peak level of ventricular signal from a peak point of ventricular signal to a time point of 200 ms.

At the time point of 200 ms, the value decreases by five (5) levels from a value corresponding to 75% of the peak level until a next ventricular signal is detected. In this fashion, the invention enables the adaptive detection method to detect or sense heartbeats at a low supply voltage.

Hereinafter the present invention will be described in more detail in conjunction with the accompanying drawings.

Throughout the drawings, the same elements will be designated with the same or similar reference signs and description thereof will be omitted.

Figure 1:
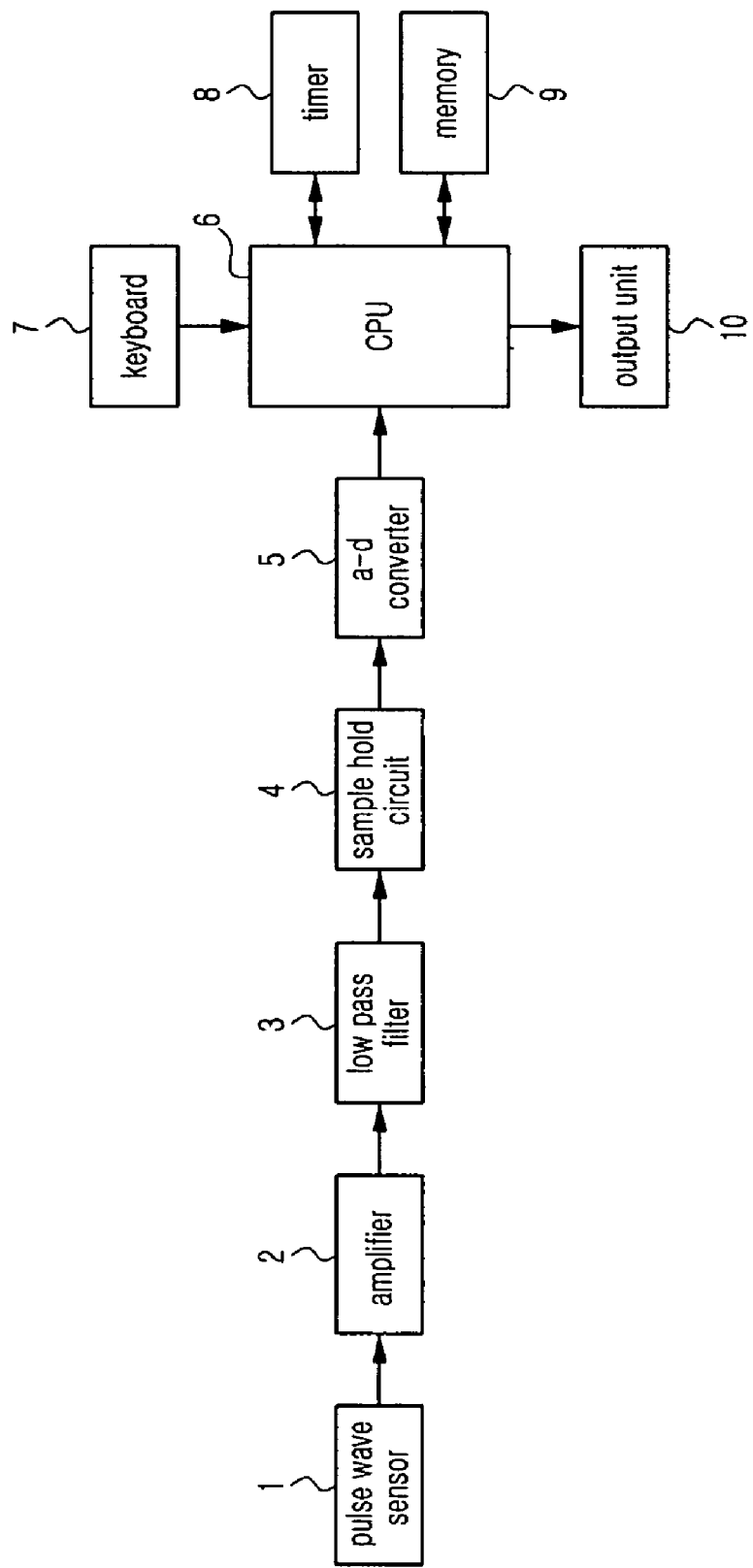
FIG. 1 is a block diagram illustrating an electric structure of a conventional pulse wave R-R interval detection system.
Figure 2:
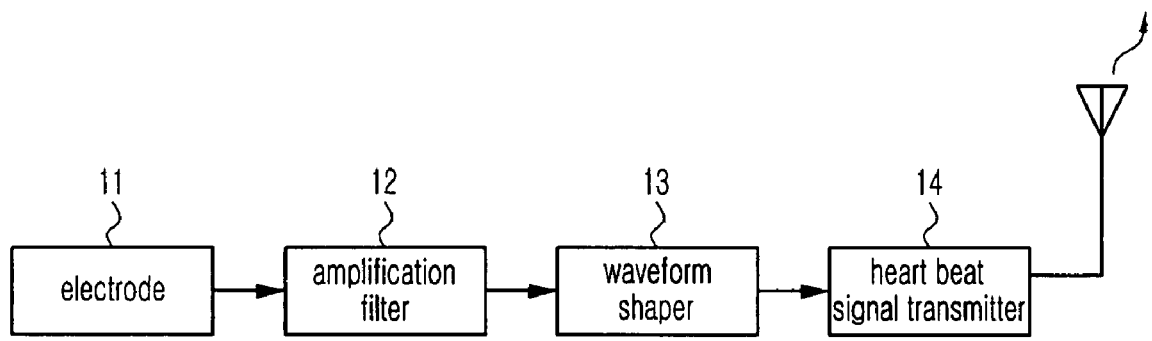
FIG. 2 is a block diagram illustrating a conventional pulse wave detection system.
Figure 3:
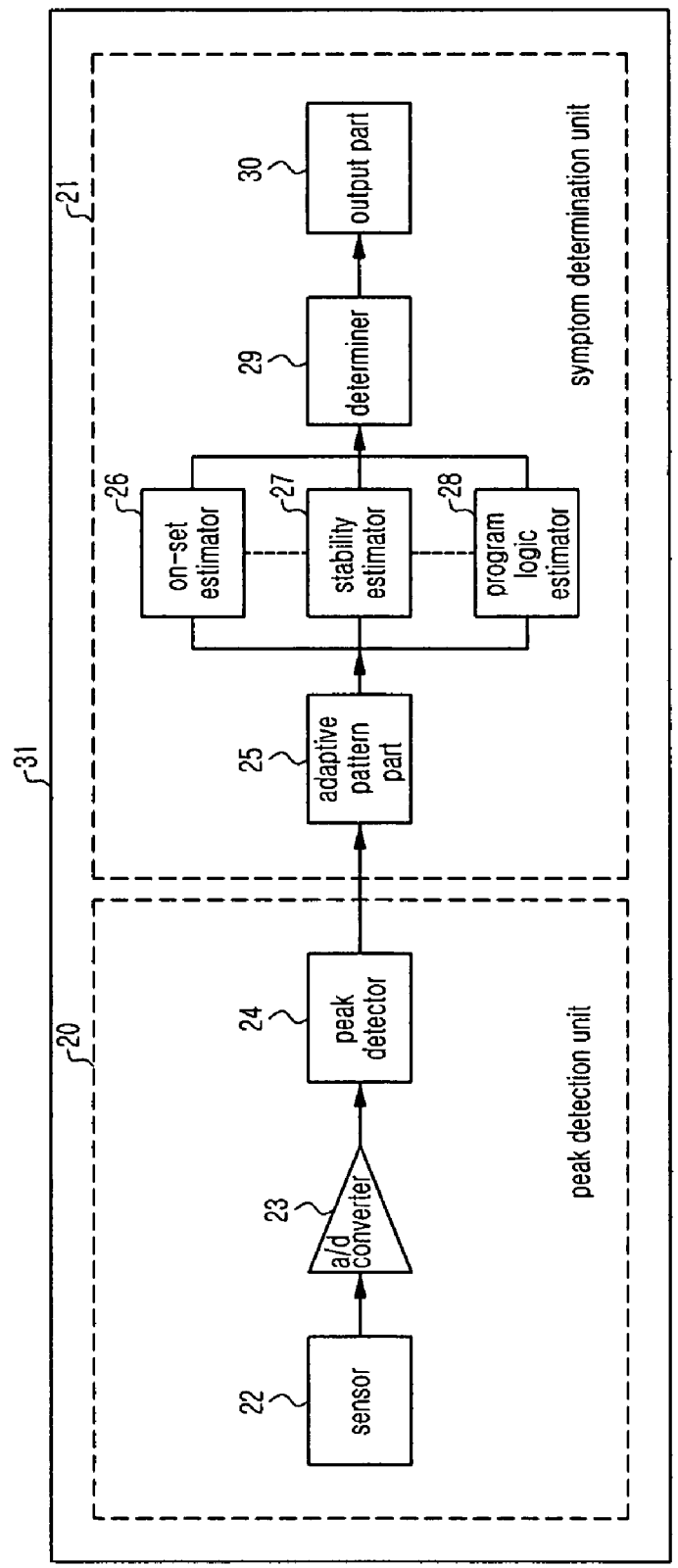
FIG. 3 is a block diagram illustrating a detection system for heartbeat peaks according to an embodiment of the invention.

FIG. 3 is a block diagram illustrating a detection system for heartbeat peaks according to an embodiment of the invention.

Referring to FIG. 3, the detection system of the invention is generally composed of a peak detection unit 20 for detecting heartbeat signals by a sensor and a symptom determination unit 21 for diagnosing any heart disease based on the peak interval of the detected heartbeat signals. The detection system is particularly composed of a sensor 22, an AD/converter 23, a peak detector 24, an adaptive pattern part 25, an on-set estimator 26, a stability estimator 27, a program logic estimator 28, a determiner 29 and an output part 30.

Accordingly, the detection system for a heartbeat peak of the invention is designed to determine heart conditions upon receiving A/D converted ventricular and atrial signals and, if there is any problem, output a proper diagnosis and prescription accordingly.

The ventricular and atrial signals are detected by the sensor 22, and then inputted into the A/D converter 23. The AD converter 23 outputs the detection signals through conversion into digital signals, and the peak detector 24 detects ventricular and atrial peaks from the digital signals and outputs the peaks to the adaptive pattern part 25.

That is, the peak detection unit 20 performs peak detection on the ventricular and atrial signals according to adaptive threshold level, and outputs 1 for peak signals and 0 for other signals.

The adaptive pattern part 25 examines the existence of five (5) types of information at a time point where the peak is detected from the output of the peak detector 24. The five types of information include peak interval, peak time, number of ventricular signals between atrial signals, number of atrial signals between ventricular signals, interval between ventricular and atrial peaks and far field R wave (or heartbeat wave). Then, the examined information is stored.

The on-set estimator 26 estimates whether or not the ventricular signal intervals have recently had any rapid change according to an output of the adaptive pattern part 25. For example, if the mean value of the latest four (4) maximum ventricular (V) peak intervals is different from that of the previous four maximum ventricular peak intervals by a reference value or more, the on-set estimator 26 sends an enable signal to the determiner 29.

The stability determiner 27 estimates whether or not the recent ventricular signal intervals are stably occurring according to outputs from the adaptive pattern part 25 and, if the latest maximum ventricular peak interval is different from the latest three maximum ventricular peak intervals by a reference value or more, sends an enable signal to the determiner 29.

The determiner 29 determines diseases in five (5) steps and outputs prescriptions in eight (8) steps. Examples of the diseases discernable by the detection system of the invention include normal, Ventricular Tachycardia (VT), Fast Ventricular Tachycardia (FVT), Ventricular Fibrillation (VF), Atrial Tachycardia-Atrial Fibrillation (AT-AF) and Fast Atrial Tachycardia-Atrial Fibrillation (FAT-AF).

The term SVT refers to supra-ventricular tachycardia, i.e., a disease of rapid heartbeat that is caused by an atrium. Since the SVT generally uses a normal conduction pathway of the heart, medication is currently used instead of forced medical treatment by medical equipment using an algorithm.

Thus, in order to discriminate SVT from other heart diseases such as VT and VF, several standards are used in a corresponding algorithm, which is estimated by the program logic estimator 28. The determiner 29 discriminatively determines various conditions such as normal condition, VF, VT, FVT via VF, FVT via VT and AT-AF based on outputs from the program logic estimator 28.

The output part 30 outputs the result in eight (8) bits so that a prescription or therapy can be presented according to the determiner 29. After the prescription is outputted from the output part 30, if a normal state is maintained, the process is enabled and the determiner 29 is switched off to perform merely peak detection.

As described above, the peak detection process of the invention is carried out in such a fashion that, after a peak is detected, the threshold level is varied to detect another peak. That is, adaptive threshold detection can be enabled. When a signal is received, the threshold is maintained at the peak level from the time point of peak detection to a time point of 200 msec. At the time point of 200 msec, the value decreases to 75% of the threshold level and then by five (5) levels each time while the next signal detection is being carried out.

If a next signal is not detected at the lowest threshold level, the threshold level is maintained at the same value as the lowest threshold level. The symptom determination unit 21 discerns detection times between peaks measured by the peak detection unit 20, which acts to detect heart signals, so as to determine or diagnose heart diseases in five steps and output prescription in eight steps according to the diseases.

That is, the invention utilizes a one-chip algorithm for measuring biopotential, available for the treatment of irregular heartbeat and blood sugar levels, in order to realize this algorithm into a hardware structure. The adaptive detection system and method for heartbeat peaks serves to diagnose diseases based on heart signals detected from a patient's heart by a sensor and enables proper treatment by outputting a prescription according to any abnormal symptom.

Figure 4:
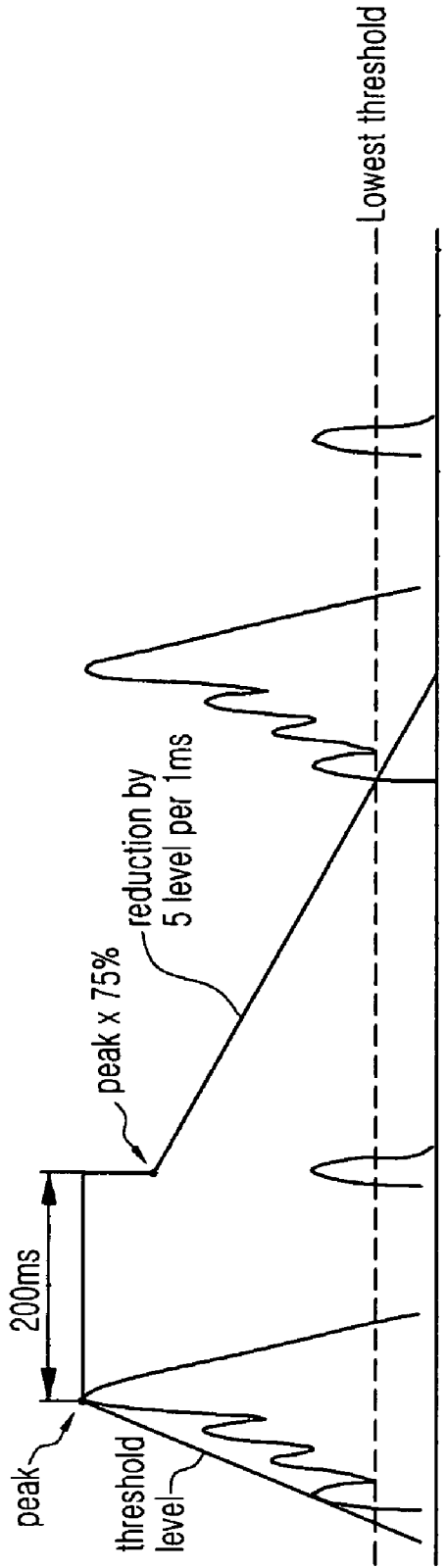
FIG. 4 is a diagram illustrating an adaptive detection algorithm for heartbeat peaks according to an embodiment of the invention.

FIG. 4 is a diagram illustrating an adaptive detection algorithm for heartbeat peaks according to an embodiment of the invention.

Referring to FIG. 4, the peak detector 24 compares the ventricular and atrial heartbeat signals, converted by the A/D converter 23, with the threshold level in order to detect a peak. An output signal from the peak detector 24 is inputted into the adaptive pattern part 25. FIG. 4 shows a process of performing detection by adaptively varying the threshold level to determine peak times, in which the minimum threshold level is a fixed value.

The minimum threshold level can realize low voltage application by optimizing a detection range of the threshold level. If the minimum threshold level is not set, the threshold level is detected from a zero (0) level. If signals are detected from a zero threshold level, peak detection should be performed for all noise signals in the vicinity of the zero level, thereby increasing power consumption.

In a reset state, the threshold level is equal with the minimum threshold level. If a signal is lower than the minimum threshold level, it is out of the threshold level range and thus not detected.

Therefore, the adaptive pattern part 25 stores the detected threshold level of the minimum threshold level or more and the peak time. That is, the peak detector 24 calculates occurrence times and peak intervals such as ventricular-to-atrial interval, ventricular-to-ventricular interval and atrial-to-ventricular interval based on the peak time inputted from the peak detector 24. Here, the peak detector 24 outputs only the peak time. Before being stored in the adaptive pattern part 25, the peak interval is separately stored and calculated, and its calculation result is stored in the adaptive pattern part 25.

The adaptive pattern part 25 receives merely the peak time, performs calculation through the foregoing procedures, stores the calculation result, and sends the calculation result to next modules. That is, the adaptive pattern part 25 outputs the calculation result to the on-set estimator 26, the stability estimator 27 and the program logic estimator 28.

The foregoing process is repeated, in which the maximum threshold level is regarded as a peak value, a peak time is stored, and the threshold level remains the same as the peak level from the time point of peak detection to the time point of 200 msec. At the time point of 200 msec, the threshold level has a value corresponding to 75% of the peak level.

The threshold level decreases by 5 levels each time, and the ventricle influences atrial heartbeat signals. With the threshold level, it is possible to selectively detect the atrial heartbeat signals by evading the influence of the ventricular heartbeat signals. Since unnecessary ventricular heartbeats are not detected during the detection of the atrial heartbeat signals, it is possible to reduce power consumption further.

Figure 5:
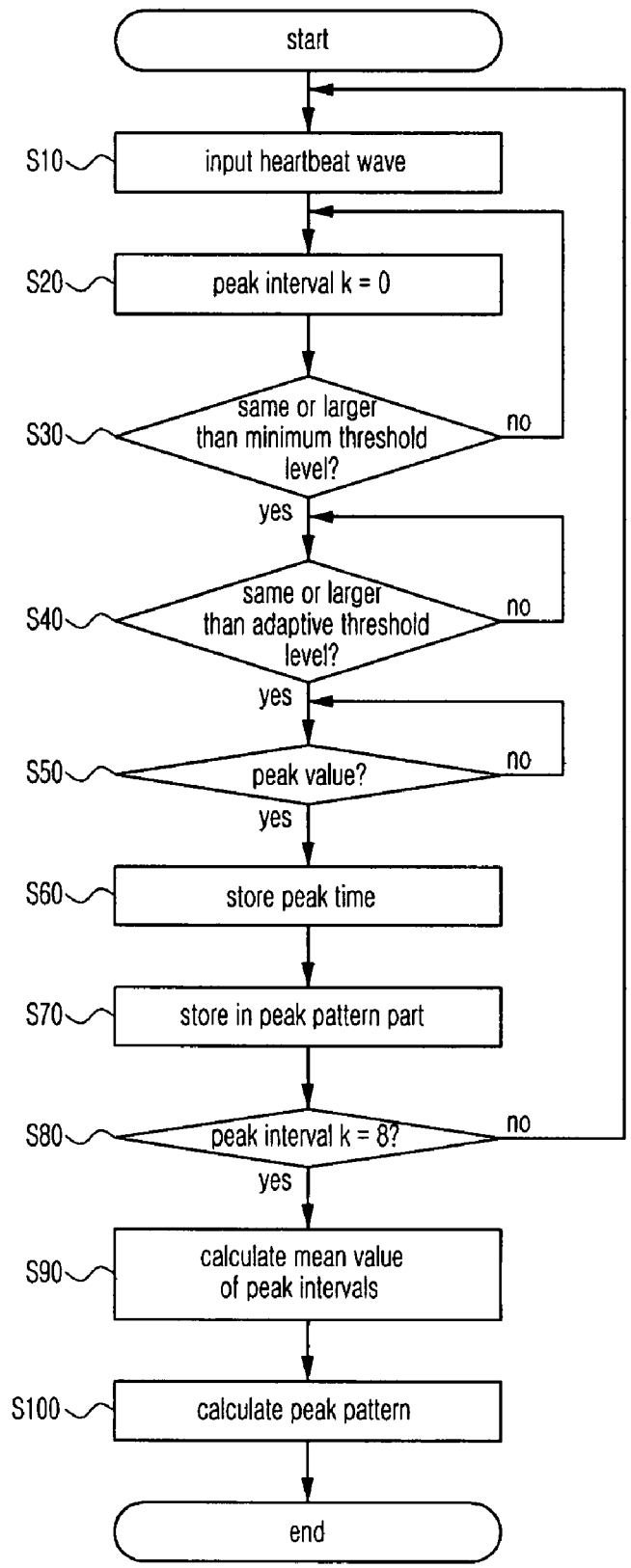
FIG. 5 is a flowchart illustrating an adaptive detection method for heartbeat peaks according to an embodiment of the invention.

FIG. 5 is a flowchart illustrating an adaptive detection method for heartbeat peaks according to an embodiment of the invention. Referring to FIG. 5, the detection system of the invention is started at its initial status to execute peak detection on heartbeat waves in S10, counts the number of inputs of peak intervals of the heartbeat waves in S20, and determines whether or not a calculated detection signal is smaller than a minimum threshold level in S30.

If the detection signal is smaller than the minimum threshold level in S30, the process returns to S20 to detect heartbeat waves again. If the detection signal is the same as or larger than the minimum threshold level, the system determines whether or not the detection signal is smaller than the adaptive threshold level in S40.

If the detection signal is smaller than the adaptive threshold level, heartbeat waves are inputted. If the detection signal is the same as or larger than the threshold level, a peak signal is detected in S50, peak time is stored in S60, and the result is stored in the peak pattern part in S70.

If it is determined that the peak signal is not a peak value in S50, detection signals are inputted again.

In S80, it is determined whether or not there are eight (8) stored peaks. If the number of stored peaks is smaller than eight, the process returns to S10 to detect the heartbeat waves again. If the number of stored peaks is eight, the mean number of the peaks is calculated in S90.

A peak pattern is produced from the mean value of the peaks in S100.

As described above, according to the adaptive detection system and method for heartbeat peaks, heartbeats can be detected at a low voltage.

Furthermore, the adaptive detection system and method for heartbeat peaks of the invention can diagnose diseases related with heart diseases and output proper prescriptions by detecting heartbeats, thereby saving social costs and preventing economic loss, restriction in active hours, reduction in productivity and so on.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. An adaptive detection system for heartbeat peaks comprising:
   means for detecting peaks of ventricular or atrial heartbeat signals according to an adaptive threshold level such that after a peak is detected, the threshold is maintained at a same peak level for a predetermined period of time, decreased to a percentage of the peak level, and then further decreased to a lowest threshold level while a next signal detection is being carried out; and
   means for determining heart conditions according to a detected peak interval,
   wherein the heart condition determining means is adapted to detect and store peak interval, peak time, number of ventricular signals between atrial signals, number of atrial signals between ventricular signals, interval between ventricular and atrial peaks and far field heartbeat wave, according to the peak detected by the peak detecting means.

2. The adaptive detection system of claim 1, wherein the heart condition determining means is adapted to output judgment on Ventricular Tachycardia (VT), Fast Ventricular Tachycardia (FVT), Ventricular Fibrillation (VF), Atrial Tachycardia-Atrial Fibrillation (AT-AF) and Fast Atrial Tachycardia-Atrial Fibrillation (FAT-AF).

3. The adaptive detection system of claim 2, wherein the peak detecting means and the heart condition determining means are realized in one chip.

4. The adaptive detection system of claim 3, wherein the chip is transplantable to treat bradyarrhythmia.

5. The adaptive detection system of claim 1, wherein the peak detecting means is adapted to adaptively detect the adaptive threshold level according to the heartbeat signal to determine peak time.

6. The adaptive detection system of claim 5, wherein the peak detecting means is adapted to set a fixed minimum threshold level and, if a detected signal does not exceed the minimum threshold level, skip peak detection therefrom.

7. The adaptive detection system of claim 6, wherein the peak detecting means detects a second peak while decreasing the threshold level by five (5) levels per second at a time point of 200 ms from a time point of peak detection.

8. An adaptive detection method for heartbeat peaks comprising steps of:
   detecting peaks of ventricular and atrial heartbeat signals according to an adaptive threshold level such that after a peak is detected, the threshold is maintained at a same peak level for a predetermined period of time, decreased to a percentage of the peak level, and then further decreased to a lowest threshold level while a next signal detection is being carried out; and
   determining heart diseases according to the peak detected in the peak detecting step,
   wherein the determining step comprises detecting and storing peak interval, peak time, number of ventricular signals between atrial signals, number of atrial signals between ventricular signals, interval between ventricular and atrial peaks and far field heartbeat wave, according to the peak detected by the peak detecting means.

9. The adaptive detection method of claim 8, wherein the detecting step comprises, upon detecting a first peak, detecting a second peak while decreasing the threshold level by five (5) levels per second at a time point of 200 ms from the detection of the first peak.

10. The adaptive detection method of claim 9, wherein the determining step comprises outputting judgment on Ventricular Tachycardia (VT), Fast Ventricular Tachycardia (FVT), Ventricular Fibrillation (VF), Atrial Tachycardia-Atrial Fibrillation (AT-AF) and Fast Atrial Tachycardia-Atrial Fibrillation (FAT-AF).

* * * * *